United States Patent [19]

Suzukamo et al.

[11] Patent Number: 4,659,864

[45] Date of Patent: Apr. 21, 1987

[54] METHOD FOR RACEMIZATION OF CHRYSANTHEMIC ACID OR ITS ESTER

[75] Inventors: Gohfu Suzukamo, Ibaraki; Masami Fukao, Shiga, both of Japan

[73] Assignee: Sumitomo Chemical Company, Ltd., Osaka, Japan

[21] Appl. No.: 744,546

[22] Filed: Jun. 14, 1985

[30] Foreign Application Priority Data

Jun. 15, 1984 [JP] Japan ............................ 59-124346
Jun. 18, 1984 [JP] Japan ............................ 59-125892

[51] Int. Cl.$^4$ ................... C07C 51/353; C07B 20/00
[52] U.S. Cl. ................................. 560/124; 562/401; 562/506
[58] Field of Search ............... 560/124; 562/401, 506

[56] References Cited

U.S. PATENT DOCUMENTS

| | | | |
|---|---|---|---|
| 3,794,680 | 2/1974 | Matsui | 562/506 |
| 3,989,750 | 11/1976 | Nagase | 562/506 |
| 4,182,906 | 1/1980 | Suzukamo | 562/506 |
| 4,473,703 | 9/1984 | Suzukamo | 562/506 |
| 4,485,257 | 11/1984 | Suzukamo | 562/506 |

FOREIGN PATENT DOCUMENTS 62979 10/1982 European Pat. Off. ............ 562/506

*Primary Examiner*—Michael L. Shippen
*Attorney, Agent, or Firm*—Birch, Stewart, Kolasch and Birch

[57] ABSTRACT

An optically active chrysanthemic acid or esters thereof are conveniently racemized with an aluminum bromide compound such as aluminum tribromide. An organic hydroperoxide should always be added to for racemization of the esters, but is not always necessary for racemization of the acid.

25 Claims, No Drawings

METHOD FOR RACEMIZATION OF CHRYSANTHEMIC ACID OR ITS ESTER

The present invention relates to a method for racemization of an optically active chrysanthemic acid or its ester of the formula:

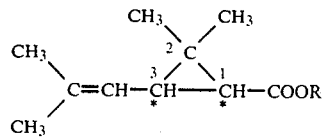

wherein R is a hydrogen atom or an alkyl group which may be substituted with a cycloalkyl group or with an aryl group, said alkyl group having the total carbon atoms of from 1 to 20 including the substituent; or a cycloalkyl group which may be substituted with an alkyl or with an alkoxy group, said cycloalkyl group having the total carbon atoms of from 5 to 20 including the substituent.

More particularly, it relates to a method for racemization of an optically active chrysanthemic acid which comprises contacting the acid with an aluminum bromide compound in the presence or absence of an organic hydroperoxide, and also a method for racemization of an optically active chrysanthemic acid ester which comprises contacting the ester with an aluminum bromide compound in the presence of an organic hydroperoxide.

The chrysanthemic acid, i.e. 2,2-dimethyl-3(2-methyl-1-propenyl)cyclopropane-1-carboxylic acid, constitutes the acid component of the esters well-known as the so-called pyrethroidal insecticides, such as pyrethrin, allethrin, phthalthrin, etc., which are utilized as low mammalian toxic, quickly effective insecticides, and is useful as intermediate for these esters.

The chrysanthemic acid has four kinds of isomers, that is, two geometrical isomers, i.e. cis and trans forms, which respectively have two kinds of optical isomers, i.e. (+) and (−) forms. It has been known that, in general, among the isomers the esters composed of a trans-form acid exhibits stronger insecticidal activity than those composed of a corresponding cis-form acid, furthermore, the esters composed of a (+)-form acid exhibits exceedingly higher activity than those composed of the corresponding (−)-isomer.

In general, the chrysanthemic acid is industrially produced as a mixture of cis and trans forms, each of which is in the form of racemic mixture, namely, as (±)-form. The optical resolution of the thus-synthesized acid by means of an optically active organic base is conducted to obtain the (+)-form acid which is utilized for the preparation of insecticidal compounds with a high activity. Wherein, the remaining (−)-isomer after the optical resolution is least useful, since the esters composed thereof are almost inactive. Accordingly, it is a problem to be solved in the production of the (+)-form acid, particularly in a commercial scale, that the (−)-form acid be racemized with a high efficiency, so as to be utilized again as the material for the optical resolution mentioned above.

The racemization of the optically active chrysanthemic acid or its ester is difficult, since it possesses two asymmetric carbon atoms, as shown above, at the 1- and 3-positions (exhibited by * marks).

Some methods for the racemization have so far been studied. Thus, a method in which (−)-trans-chrysanthemic acid is oxidized at its $C_3$-substituted isobutenyl group to convert into a keto-alcohol group, and the acid group at the $C_1$-position is converted into a lower alkyl ester, which is then subjected to a reaction with an alkali metal alcoholate in a solvent (U.S. Pat. No. 3,282,984); a method in which (−)-trans-chrysanthemic acid is irradiated with ultraviolet rays in the presence of a photosensitizer (U.S. Pat. No. 3,657,086); a method in which optically active chrysanthemic acid is converted into the corresponding acid halide and then contacted with a Lewis acid (U.S. Pat. Nos. 3,989,750 and 4,182,906); and a method in which optically active chrysanthemic acid is converted into an acid anhydride and then contacted with an iodine (U.S. Pat. No. 4,485,257) have been known.

As a result of an extensive study, the inventors have now found that optically active chrysanthemic acid can be racemized conveniently by the treatment with an aluminum bromide compound and that the presence of an organic hydroperoxide greatly facilitates the racemization to have it proceeded more readily and in high yield. Furthermore, the inventors have also found that optically active chrysanthemic acid ester of the formula (I) can be racemized conveniently and in high yield by the treatment with an aluminum bromide compound in the presence of an organic hydroperoxide. This invention is based on such finding.

According to the present invention, the optically active chrysanthemic acid or its ester can be racemized readily and in high yield and the method of the present invention is very convenient for the racemization particularly in commercial scale. Moreover, the present invention enables the direct utilization of (−)-chrysanthemic acid or its ester, which was separated off in the procedures of optical resolutions, with high efficiency.

In the method of the present invention, the use of an organic hydroperoxide brings about a remarkable reduction in an amount of an aluminum bromide compound needed for the racemization of chrysanthemic acid as well as a considerable reduction in the reaction time.

This racemization method always gives the trans-rich reaction product regardless of the isomeric composition of the starting material. Since the insecticidal activity of the pyrethroidal esters in the trans form is generally higher than that of the corresponding esters in the cis form, the above characteristic feature of the racemization method is of great advantage. Thus, the racemization method may be also applied to the conversion of the racemic cis isomer or of a mixture of the racemic cis and trans isomers of the acid or its ester to the corresponding racemic trans-rich isomer.

The method of the present invention will more fully be described hereinafter.

In the present invention, any of the four optical isomers of chrysanthemic acid or its ester can be used solely or in mixtures of an optional proportion as the starting material. The starting material of any degree of the optical purity can be employed. Needless to say, however, employment of the starting material of (−)-form or rich in (−)-form makes the object of the present invention significant.

As the chrysanthemic acid ester for example, there may be illustrated methyl chrysanthemate, ethyl chrysanthemate, propyl chrysanthemate, butyl chrysanthemate, cyclohexyl chrysanthemate, cyclohexylmethyl chrysanthemate, benzyl chrysanthemate and the like.

As the aluminum bromide compound used in the method of the present invention, there may be typically illustrated aluminum tribromide. The aluminum bromide compound is usually used within the range from 1/1000 to ¼ mole based on mole of the starting material to be treated. Preferably, the amount is 1/50 to ¼ mole when chrysanthemic acid is racemized in the absence of an organic hydroperoxide and 1/200 to 1/20 mole in the presence of an organic hydroperoxide, based on mole of the chrysanthemic acid to be treated. When chrysanthemic acid ester is racemized, the amount of the aluminum bromide compound is preferably 1/500 to 1/5 mole based on mole of the chrysanthemic acid ester.

As the organic peroxide, there may be illustrated as below.

(1)
Aliphatic hydroperoxide
Hydroperoxide produced by oxidation of ethers such as tetrahydrofuran, dioxane or the like,
tert-Butyl hydroperoxide,
1,1,3,3-Tetramethyl butyl hydroperoxide,
p-Menthane hydroperoxide, etc.

(2)
Aromatic hydroperoxide
Cumene hydroperoxide
Diisopropylbenzene hydroperoxide, etc.

The amount of the organic hydroperoxide to be used, in general, is a range from 1/10 to 5 mol, preferably ¼ to 2 mol, based on mol of the aluminum bromide compound used.

In carrying out the present racemization reaction, an inert solvent may preferably be used. For such solvents, there may be illustrated aromatic hydrocarbons and their halide compounds, ethers, etc.

The reaction temperature may generally be chosen arbitrarily within the range from −30° C. to 100° C.

The reaction time is more or less associated with the amount of materials to be used and the reaction temperature. Usually the object would be well achieved within a period of time ranging from a few minutes to 10 hours.

In carrying out the present racemization reaction in the presence of organic hydroperoxide, the following procedure is generally employed. One is the procedure in which an aluminum bromide compound is added into a mixture of the starting material to be treated and an organic hydroperoxide in a solvent, and the other is the procedure in which an organic hydroperoxide and an aluminum bromide compound are in parallel added into the starting material to be treated in a solvent.

The proceeding of the reaction can be checked by any of measurement of the optical rotation, gas-chromatography, etc.

As described in above, by the method of the present invention, the racemization of the (−)-isomer of the optically active chrysanthemic acid or its ester can be readily and economically accomplished in commercial scale. The thus racemized product may be subjected to optical resolution procedures to obtain the useful (+)-isomer of chrysanthemic acid or its ester.

Moreover, the racemization method of the present invention can be also applied to the conversion of the racemic cis isomer or of a mixture of the racemic cis and trans isomers of the chrysanthemic acid or its ester to the corresponding racemic trans-rich isomer being more useful.

The method of the present invention will be further illustratively shown in the following examples.

EXAMPLE 1

In a 50 ml flask, there were charged (−)-cis-chrysanthemic acid (2.0 g) and dioxane (17.5 g) under nitrogen. A solution of aluminum bromide (0.063 g) in dioxane (0.5 g) was added thereto at 15°–20° C. with stirring. After 30 minutes, water (0.5 g) was added to the reaction mixture with stirring. The solution was concentrated under reduced pressure. Hexane was added to the residue. The solution was washed with dil. hydrochloric acid and the aqueous layer was separated. Ten % aqueous sodium hydroxide solution (7.1 g) was added to the organic layer at 40° C. with stirring and the aqueous layer was separated. The aqueous layer was acidified with diluted sulfuric acid and extracted with toluene. The toluene layer was washed with water and concentrated. The residue was distilled (b.p. 110°–119° C./2.5 mmHg) to obtain 1.88 g of distillate. The IR spectrum of the product was identical with that of chrysanthemic acid. The composition of the optical isomers in the product was determined by gas chromstography after conversion into (+)-2-octyl ester. The result was as follows: (+)-cis, 3.0%; (−)-cis, 4.9%; (+)-trans, 46.0%; (−)-trans, 46.1%.

EXAMPLE 2

In a 50 ml flask, there were charged chrysanthemic acid [composition: (+)-cis, 3.0%; (−)-cis, 22.0%; (+)-trans, 11.8%; (−)-trans, 63.2%] (5.0 g) and toluene (11.7 g) under nitrogen. Aluminum bromide (0.12 g) was added thereto at 15°–20° C. with stirring. After 30 minutes, the composition of the optical isomers of chrysanthemic acid in the reaction solution was determined by the same method as described in Example 1. The composition was as follows: (+)-cis, 2.9%; (−)-cis, 4.6%; (+)-trans, 26.5%; (−)-trans, 65.9%).

EXAMPLE 3

In a 50 ml flask, there were charged (−)-cis-chrysanthemic acid (2.0 g), dioxane (17.5) and t-butyl hydroperoxide (0.011 g) under nitrogen. A solution of aluminum bromide (0.032 g) in dioxane (0.5 g) was added thereto at 15°–20° C. with stirring. After 30 minutes, water (0.5 g) was added to the reaction mixture with stirring. The reaction mixture was treated in the same manner as described in Example 1 and 1.91 g of chrysanthemic acid was obtained. The composition was as follows: (+)-cis, 3.3%; (−)-cis, 4.2%; (+)-trans, 46.2%; (−)-trans, 46.2%.

EXAMPLE 4

In a 50 ml flask, there were charged chrysanthemic acid [composition: (+)-cis, 3.0%; (−)-cis, 22.0%; (+)-trans, 11.8%; (−)-trans, 63.2%] (5.0 g), toluene (11.7 g) and t-butyl hydroperoxide (0.02 g) under nitrogen. Aluminum bromide (0.12 g) was added thereto at 15°–20° C. with stirring. After 30 minutes, the composition of the optical isomers of chrysanthemic acid in the reaction solution was determined by the same method as described in Example 1. The composition was as follows: (+)-cis, 2.3%; (−)-cis, 2.4%; (+)-trans, 45.6%; (−)-trans, 49.7%. After 1 hr, dil. hydrochloric acid (5 g) was added to the reaction mixture and stirred. Ten % aqueous sodium hydroxide solution (17.9 g) was added to the organic layer at 40° C. with stirring and the aqueous layer was separated. The aqueous layer was acidified with diluted sulfuric acid and extracted with toluene. The toluene layer was washed with water and concentrated. The residue was distilled (b.p. 110–119° C./2.5 mmHg) to obtain 4.8 g of distillate. The IR spectrum of the product was identical with that of chrysanthemic acid. The composition of the optical isomers in the product was determined by gas chromstography after conversion into (+)-2-octyl ester. [composition: (+)-cis, 2.4%; (−)-cis, 2.4%; (+)-trans, 46.7%; (−)-trans, 48.5%].

EXAMPLES 5-7

Procedure was carried out in the same manner as in Example 2. The reaction conditions and the results were summarized in the following Table.

| Example No. | Chrysanthemic acid (g) [Composition, (+)-cis: (−)-cis:(+)-trans:(−)-trans] | <Reaction Conditions> toluene (g) | t-BuOOH (g) | AlBr₃ (g) | temp. (°C.) | time (min.) | <Results> Composition of optical isomers (%) (+)-cis | (−)-cis | (+)-trans | (−)-trans |
|---|---|---|---|---|---|---|---|---|---|---|
| 5 | 1.0 (0:100:0:0) | 9.0 | 0.005 | 0.009 | 15~20 | 10 | 2.3 | 5.1 | 46.3 | 46.3 |
| 6 | 7.3 (3.0:22.0:11.8:63.2) | 17.1 | 0.09 | 0.29 | 0 | 30 | 2.6 | 2.6 | 45.1 | 49.7 |
| 7 | 7.6 (3.0:22.0:11.8:63.2) | 17.7 | 0.10 | 0.30 | 40 | 30 | 2.7 | 2.7 | 46.2 | 48.4 |

EXAMPLE 8

In a 50 ml flask, there were charged (±)chrysanthemic acid (cis:trans=70.0:30.0) (5.0 g) and toluene (25.0 g) under nitrogen. Aluminum bromide (0.13 g) in toluene (1.3 g) was added thereto at 18°–22° C. with stirring and stirred for 1 hour. Ten % hydrochloric acid (2.0 g) was added to the reaction mixture and the aqueous layer was removed. Ten % aqueous sodium hydroxide solution (17.9 g) was added to the organic layer at 40° C. with stirring and the aqueous layer was separated. The aqueous layer was acidified with diluted sulfuric acid and extracted with toluene. The toluene layer was washed with water and concentrated. The residue was distilled (b.p. 110°–119° C./2.5 mmHg) to obtain 4.6 g of chrysanthemic acid. The composition of the isomers in the product was determined by gas chromstography; cis:trans=7.0:93.0.

EXAMPLE 9

In a 50 ml flask, there were charged (±)-chrysanthemic acid (cis:trans=70.0:30.0) (5.0 g), toluene (25.0 g) and t-butyl hydroperoxide (0.030 g) under nitrogen. Aluminum bromide (0.09 g) in toluene (1.3 g) was added thereto at 18°–22° C. with stirring and stirred for 1 hour. The reaction mixture was treated in the same manner as described in Example 8 and 4.7 g of chrysanthemic acid was obtained, cis:trans=6.0:94.0.

EXAMPLE 10

In a 50 ml flask, there were charged (±)-cis-chrysanthemic acid (1.0 g), chlorobenzene (8.5 g) and cumene hydroperoxide (0.018 g) under nitrogen. Aluminum bromide (0.032 g) in chlorobenzene (0.5 g) was added thereto at 15°–20° C. with stirring and stirred for 30 min. Hexane (5.0 g) and 10% hydrochloric acid (1.0 g) were added to the reaction mixture and the organic layer was separated. The content of chrysanthemic acid in the organic layer was analyzed by gas chromatography to be 0.984 g. The isomeric ratio (cis:trans) was 6.6:93.4.

EXAMPLE 11

In a 30 ml flask, there were charged ethyl chrysanthemate [composition: (+)-cis, 2.4%; (−)-cis, 15.3%; (+)-trans, 12.1%; (−)-trans, 70.2%] (2.0 g), dioxane (8.0 g) and t-butyl hydroperoxide (0.05 g) under nitrogen. Aluminum bromide (0.16 g) was added thereto at 20° C. with stirring. The reaction mixture was stirred for 1 hour. A small amount of water was added to the reaction mixture to decompose the catalyst and the resulting mixture was concentrated under reduced pressure. Toluene (10 ml) was added to the residue and the mixture was washed with 20% hydrochloric acid (1 ml), 10% sodium hydroxide solution (1 ml), and saturated sodium chloride solution (1 ml), successively. The solvent was evaporated under reduced pressure to leave a residue (1.95 g). The residue was distilled (b.p. 85°–88° C./10 mmHg) to obtain a product (1.87 g). The IR spectrum of the product was identical with that of ethyl chrysanthemate. Then the product was hydrolyzed by usual method to give chrysanthemic acid (b.p. 110°–119° C./2.5 mmHg, 1.57 g). The composition of the optical isomers of the acid was determined by the same method as described in Example 1. The result was as follows: (+)-cis, 2.9%; (−)-cis, 3.2%; (+)-trans, 46.2%; (−)-trans, 47.7%.

EXAMPLE 12

In a 30 ml flask, there were charged ethyl chrysanthemate [composition: (+)-cis, 2.4%; (−)-cis, 15.3%; (+)-trans, 12.1%; (−)-trans, 70.2%] (2.0 g) and toluene (6.0 g) under nitrogen. Aluminum bromide (0.27 g) in toluene (1.0 g) and t-butyl hydroperoxide (0.09 g) in toluene (1.0 g) were added dropwise simultaneously thereto at 20° C. with stirring under nitrogen. After stirring for 1.5 hours at the same temperature, the reaction mixture was treated in the same manner as described in Example 11 to give a product (b.p. 85°–88° C./10 mmHg, 1.68 g). The IR spectrum of the product was identical with that of ethyl chrysanthemate. A small amount of the product was hydrolyzed and then converted into (+)-2-octyl ester. The composition of the optical isomers was determined by gas chromatography: (+)-cis, 3.1%; (−)-cis, 2.9%; (+)-trans, 44.4%; (−)-trans, 49.6%.

EXAMPLE 13

In a 30 ml flask, there were charged n-butyl chrysanthemate [composition: (+)-cis, 1.1%; (−)-cis, 18.5%; (+)-trans, 3.8%; (−)-trans, 76.6%] (2.0 g) and chlorobenzene (6.0 g) under nitrogen. Aluminum bromide (0.26 g) in chlorobenzene (1.0 g) and t-butyl hydroperoxide (0.09 g) in chlorobenzene (1.0 g) were added dropwise simultaneously thereto at 30° C. with stirring under nitrogen. After stirring for 2 hours at the same temperature, the reaction mixture was treated in the same manner as described in Example 11 to give a product (b.p. 105°–106° C./2 mmHg, 1.62 g). The IR spectrum of the product was identical with that of n-butyl chrysanthemate. A small amount of the product was hydrolyzed and then the composition of the optical isomers was determined by gas chromatography: (+)-cis, 4.9%; (−)-cis, 5.1%; (+)-trans, 42.4%; (−)-trans, 47.6%.

EXAMPLE 14

In a 30 ml flask, there were charged (−)-cis ethyl chrysanthemate (1.0 g), dioxane (8.0 g) and t-butyl hydroperoxide (0.0092 g) under nitrogen. Aluminum bromide (0.027 g) in dioxane (0.5 g) was added thereto at 15°–20° C. with stirring. After 1 hour, water was added to the reaction mixture. The solution was concentrated under reduced pressure. Hexane was added to the residue. The solution was washed with dil. hydrochloric acid, dil. sodium hydroxide solution and saturated sodium chloride solution, successively. The solution was dried over anhydrous sodium sulfate, and the solvent was removed in vacuo to give an oily product (1.0 g). Gas chromatographic analysis showed that this product contained 0.947 g of ethyl chrysanthemate. A small amount of the product was hydrolyzed. The composition of the optical isomers was determined by gas chromatography: (+)-cis, 2.9%; (−)-cis, 8.6%; (+)-trans, 43.4%; (−)-trans, 45.1%.

EXAMPLE 15

In a 30 ml flask, there were charged (±)-cis ethyl chrysanthemate (1.0 g), dioxane (8.0 g) and t-butyl hydroperoxide (0.0092 g) under nitrogen. Aluminum bromide (0.027 g) in dioxane (0.5 g) was added thereto at 20° C. with stirring. After 1 hour, the reaction mixture was treated in the same manner as described in Example 14 to give an oily product (1.0 g). Gas chromatographic analysis showed that this product contained 0.947 g of ethyl chrysanthemate. The composition was determined by gas chromatography: cis, 11.4%; trans, 88.6%.

EXAMPLE 16

In a 30 ml flask, there were charged (±)-ethyl chrysanthemate (cis:trans=35:65) (2.0 g), toluene (8.0 g) and t-butyl hydroperoxide (0.046 g) under nitrogen. Aluminum bromide (0.14 g) in toluene (0.5 g) was added thereto at 15°–21° C. with stirring. After 1 hour, dil. hydrochloric acid was added to the reaction mixture to quench the catalyst. The aqueous layer was separated and the organic layer was washed with dil. sodium hydroxide solution and saturated sodium chloride solution, successively. The solution was dried over anhydrous sodium sulfate, and the solvent was removed in vacuo to give an oily product (2.0 g). Distillation of the product afforded 1.84 g of a distillate (b.p. 85°–88° C./10 mmHg). The IR spectrum was identical with that of ethyl chrysanthemate. The composition was determined by gas chromatography: cis, 7.2%; trans, 92.8%.

We claim:

1. A method for racemization of an optically active chrysanthemic acid, which comprises contacting said acid with an aluminum bromide compound.

2. The method according to claim 1, wherein the contact is effected in the presence of an organic hydroperoxide.

3. The method according to claim 1, wherein the aluminum bromide compound is aluminum tribromide.

4. A method for racemization of an optically active chrysanthemic acid ester of the formula:

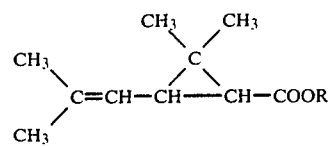

wherein R is selected from the group consisting of an alkyl group and a cycloalkyl group, said alkyl group may be substituted with a group selected from the group consisting of a cycloalkyl group and an aryl group, with alkyl group having from 1 to 20 total carbon atoms including the substituent, said cycloalkyl group may be substituted with a group selected from the group consisting of an alkyl group and an alkoxy group, said cycloalkyl group having from 5 to 20 total carbon atoms including the substituent, said method comprising:

contacting said ester with an aluminum bromide compound in the presence of an organic hydroperoxide.

5. The method according to claim 4, wherein the aluminum bromide compound is aluminum tribromide.

6. A method for converting isomers selected from the group consisting of a racemic cis isomer and a mixture of the racemic cis and trans isomers of chrysanthemic acid into the corresponding racemic trans-rich isomer, said method comprising:

contacting said acid with an aluminum bromide compound.

7. The method according to claim 6, wherein the contact is effected in the presence of an organic hydroperoxide.

8. The method according to claim 6, wherein the aluminum bromide compound is aluminum tribromide.

9. A method for the conversion of isomers selected from the group consisting of a racemic cis isomer and a mixture of racemic cis and trans isomers of chrysanthemic acid ester of formula:

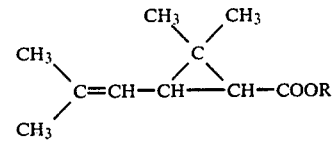

wherein R is selected from the group consisting of an alkyl group and a cycloalkyl group, said alkyl group may be substituted with a group selected from the group consisting of a cycloalkyl group and an aryl group, said alkyl group having from 1 to 20 total carbon atoms including the substituent, said cycloalkyl group may be substituted with a group selected from the group consisting of an alkyl group and an alkoxy group, said cycloalkyl group having from 5 to 20 total carbon atoms including the substituent, into the corresponding racemic trans-rich isomer, said method comprising:

contacting said ester with an aluminum bromide compound in the presence of an organic hydroperoxide.

10. The method according to claim 9, wherein the aluminum bromide compound is aluminum tribromide.

11. The method according to claim 2, wherein the aluminum bromide compound is aluminum tribromide.

12. The method according to claim 7, wherein the aluminum bromide compound is aluminum tribromide.

13. The method according to claim 4, wherein the chrysanthemic acid ester is selected from the group consisting of methyl chrysanthemate, ethyl chrysanthemate, propyl chrysanthemate, butyl chrysanthemate, cyclohexyl chrysanthemate, cyclohexylmethyl chrysanthemate and benzyl chrysanthemate.

14. The method according to claim 1, wherein the amount of aluminum bromide is from 1/1000 to ¼ mol based on the molar amount of the chrysanthemic acid.

15. The method according to claim 14, wherein the amount of aluminum bromide is 1/50 to ¼ mol based on the molar amount of the chrysanthemic acid.

16. The method according to claim 2, wherein the amount of aluminum bromide is from 1/200 to 1/20 mol based on the molar amount of the chrysanthemic acid.

17. The method according to claim 4, wherein the amount of aluminum bromide is 1/500 to 1/5 mol based on the molar amount of chrysanthemic acid ester.

18. The method according to claim 2, wherein the organic hydroperoxide is selected from the group consisting of hydroperoxide, tert-butyl hydroperoxide, 1,1,3,3,-tetramethyl butyl hydroperoxide, p-menthane, cumene hydroperoxide and diisopropylbenzene hydroperoxide.

19. The method according to claim 2, wherein the amount of the organic hydroperoxide is from 1/10 to 5 mol based on the molar amount of aluminum bromide.

20. The method according to claim 19, wherein the amount of organic hydroperoxide is ¼ to 2 mol.

21. The method according to claim 1, wherein a solvent selected from the group consisting of aromatic hydrocarbons, aromatic hydrocarbon halides and aromatic hydrocarbon ethers is added.

22. The method according to claim 1, wherein the reaction temperature is within the range from $-30$ C. to $100$ C.

23. The method of claim 1, wherein the reaction time is up to about 10 hours.

24. The method of claim 6, wherein the temperature is within the range from $-30$ C. to $100$ C.

25. A method for racemization of optically active chrysanthemic acid, which comprises:
   contacting said optically active chrysanthemic acid with an aluminum bromide compound thereby racemizing said optically active chrysanthemic acid.

* * * * *